United States Patent
Comhaire et al.

(10) Patent No.: US 9,938,495 B2
(45) Date of Patent: Apr. 10, 2018

(54) COMPOSITION COMPRISING CRYOPRESERVATION MEDIUM AND STEM CELLS OBTAINED BY SLOW-FREEZING

(71) Applicant: FERTIPRO N.V., Beernem (BE)

(72) Inventors: Sven Comhaire, Nieuwpoort (BE); Björn Comhaire, Lotenhulle (BE); Frank Eertmans, Beernem (BE); Veerle Bogaert, Beernem (BE)

(73) Assignee: FERTIPRO N.V., Beernem (BE)

( * ) Notice: Subject to any disclaimer, the term of this patent is extended or adjusted under 35 U.S.C. 154(b) by 0 days.

(21) Appl. No.: 15/255,175

(22) Filed: Sep. 2, 2016

(65) Prior Publication Data

US 2016/0369227 A1 Dec. 22, 2016

Related U.S. Application Data

(62) Division of application No. 14/574,748, filed on Dec. 18, 2014, now Pat. No. 9,458,424.

(30) Foreign Application Priority Data

Dec. 19, 2013 (EP) ..................................... 13198441

(51) Int. Cl.
*A01N 1/02* (2006.01)
*C12N 5/00* (2006.01)
*C12N 5/077* (2010.01)
*C12N 5/0775* (2010.01)

(52) U.S. Cl.
CPC ......... *C12N 5/0018* (2013.01); *A01N 1/0221* (2013.01); *C12N 5/0656* (2013.01); *C12N 5/0668* (2013.01); *C12N 2500/05* (2013.01); *C12N 2500/30* (2013.01); *C12N 2500/34* (2013.01); *C12N 2500/90* (2013.01)

(58) Field of Classification Search
None
See application file for complete search history.

(56) References Cited

U.S. PATENT DOCUMENTS

| | | | |
|---|---|---|---|
| 8,293,462 B2 * | 10/2012 | Eto | A01N 1/02 435/1.1 |
| 9,458,424 B2 * | 10/2016 | Comhaire | A01N 1/0221 |
| 2007/0087322 A1 | 4/2007 | Eto et al. | |
| 2008/0247915 A1 * | 10/2008 | Cecchi | A01N 1/02 422/400 |
| 2009/0123905 A1 | 5/2009 | Eto et al. | |
| 2009/0130756 A1 | 5/2009 | Klann | |
| 2009/0142830 A1 * | 6/2009 | Yamashiro | A01N 1/0221 435/366 |
| 2012/0128641 A1 | 5/2012 | Austen, Jr. | |
| 2013/0059286 A1 * | 3/2013 | Chang | C12N 5/0665 435/1.3 |
| 2015/0017628 A1 | 1/2015 | Gibson | |
| 2015/0320031 A1 | 11/2015 | Andreasen | |

OTHER PUBLICATIONS

Wang, H. et al. Cryopreservation of Umbilical Cord Blood Derived Mesenchymal Stem Cells Without DMSO. CryoLetters 32(1)81-88, 2011.*
Liu, Y. et al. Cryopreservation of Human Bone Marrow Derived Mesenchymal Stem Cells with Reduced DMSO and Well Defined Freezing Solutions. American Institute of Chemical Engineers 26:1635-1643, Jun. 2010.*
Demirci U. et al. Cell Encapsulating Droplet Vitrification. Lab on a Chip 7(11)1428-1433, Jul. 2007.*
Chen S. et al. Observational Clinical Followup of Oocyte Cryopreservation Using a Slow Freezing Method with 1,2-Propanediol Plus Sucrose Followed by ICSI. Human Reproduction 20(7)1975-2005, Mar. 2005.*
He, X. et al. Vitrification by Ultra-Fast Cooling at a Low Concentration of Cryoprotectants in a Quartz Micro-Capillary. Cryobiology 56(3)223-32, Mar. 2008.*
Communication European Search Report dated Feb. 25, 2014 in connection with European Patent Application No. 13198441.1, 6 pages.
Liu Y et al., entitled "Cryopreservation of human bone marrow-derived mesenchymal stem cells with reduced dimethylsulfoxide and well-defined freezing solutions," Biotechnology Progress, vol. 26, No. 6, Nov. 15, 2010, pp. 1635-1643.
Katkov I I et al., entitled "DMSO-Free Programmed Cryopreservation of Fully Dissociated and Adherent Human Induced Pluripotent Stem Cells," Stem Cells International, vol. 18, No. 5-6, Jan. 1, 2011, 8 pages.
Communication European Search Report dated Mar. 5, 2015 in connection with European Patent Application No. 14198971.5, 6 pages.
Wang H et al., entitled "Cryopreservation of Umbilical Cord Blood Derived Mesenchymal Stem Cells Without DMSO," CryoLetters 32(1)81-88, Jan. 2011.
Hreinsson J et al., entitled "Cryopreservation of Follicles in Human Ovarian Cortical Tissue," Human Reproduction 18(11) 2420-2428, Nov. 2003.

* cited by examiner

*Primary Examiner* — Ralph J Gitomer
(74) *Attorney, Agent, or Firm* — Amster, Rothstein & Ebenstein LLP

(57) ABSTRACT

Cryopreserved stem cells with high cell viability after thawing were obtained by slow freezing using a DMSO-free cryopreservation medium. Stem cells and/or progenitor cells thereof are contacted with a DMSO-free cryopreservation medium, comprising between 4 v/v % and 25 v/v % of propylene glycol and between 1.0 w % and 10 w % of a sugar; and are subsequently subject to a slow-freezing process. Optionally, the cryopreservation medium may comprise serum albumin and/or hyaluronic acid.

8 Claims, 2 Drawing Sheets

COMPOSITION COMPRISING CRYOPRESERVATION MEDIUM AND STEM CELLS OBTAINED BY SLOW-FREEZING

This application is a divisional of U.S. patent application Ser. No. 14/574,748, filed Dec. 18, 2014, now U.S. Pat. No. 9,458,424 B2, issued Oct. 4, 2016, which claims priority to European Patent Application No. 13198441.1, filed Dec. 19, 2013, the contents of which are herein incorporated by reference in their entirety.

FIELD OF THE INVENTION

Provided herein are tools and methods for the cryopreservation of cells, more particularly stem cells and/or progenitor cells thereof. Further provided herein are cryopreservation media and the use thereof for the cryopreservation of stem cells and/or progenitor cells thereof.

BACKGROUND OF THE INVENTION

Cryopreservation or cryoconservation is a process whereby cells, whole tissues, or any other substances susceptible to damage caused by chemical reactivity or time are preserved by cooling to sub-zero temperatures. Bringing cells to such low temperatures can result in damage caused by the formation of ice during freezing. To avoid this, cryopreservation typically relies on coating the material to be frozen with a class of molecules termed cryoprotectants or cryoprotective agents (CPAs). More particularly, prior to cryopreservation (CP), the material to be frozen is typically placed into a cryopreservation medium, containing one or more CPAs. A commonly used CPA is dimethylsulfoxide (DMSO). However, DMSO is toxic, and even if the cells are washed to remove the DMSO, it cannot be excluded that some remains around the cells.

Cryopreservation methods are critical in the context of stem cell therapy to allow cells that are harvested or cultured to be maintained until use without loss of quality. A number of publications report side effects in patients receiving cellular transplants as a result of DMSO toxicity. Other cryoprotectants have been investigated, but not one has come out as effective as DMSO, in particular for slow freezing cryopreservation methods. Accordingly, the use of DMSO-based cryopreservation media remain popular in use. Moreover it appears that the efficacy of the cryoprotectant may be dependent on the cell type.

Stem cells are undifferentiated biological cells which are able to renew themselves through mitotic cell division and can differentiate into specialized cell types. Stem cells have a wide (potential) application in the treatment of human and animal conditions. Stem cells are divided into different types based on their potency. Pluripotency refers to the ability of a stem cell to differentiate into cells of any of the three germ layers: endoderm (interior stomach lining, gastrointestinal tract, the lungs), mesoderm (muscle, bone, blood, urogenital), or ectoderm (epidermal tissues and nervous system). The only natural pluripotent cells are embryonic stem cells. Induced pluripotent stem cells (iPSCs) are obtained by artificial expression of certain genes in adult somatic cells which allows the cell to become pluripotent.

Multipotency describes stem cells which have the potential to differentiate into multiple but limited cell types. A hematopoietic stem cell can differentiate into different blood cell types but not into cells of other organs such as brain or bone tissue. The increased level of differentiation in multipotent cells, while limiting its therapeutic application to a disease of the corresponding cell type, is believed to limit the risk of tumor formation.

There is a need for improved cryopreservation media and methods for the cryopreservation of stem cells and/or progenitor cells, in particular for slow-freezing cryopreservation methods.

SUMMARY OF THE INVENTION

Provided herein are tools and methods for the cryopreservation of such as but not limited to multipotent cells, and/or progenitor cells thereof. More particularly provided herein are cryopreservation media and the use thereof for the cryopreservation of stem cells and/or progenitor cells.

The application thus relates to the use of a cryopreservation medium for the cryopreservation of stem cells or progenitor cells thereof, wherein said medium does not comprise dimethylsulfoxide (DMSO) or an arabinogalactan and comprises between 4 v/v % and 25 v/v % of propylene glycol. In particular embodiments said medium does not comprise dimethylsulfoxide (DMSO) and comprises between 4 v/v % and 25 v/v % of propylene glycol, and between 1.0 w % and 10 w % of one or more sugars. In further particular embodiments, the medium does not comprise dimethylsulfoxide (DMSO) or an arabinogalactan and comprises between 4 v/v % and 25 v/v % of propylene glycol, and between 1.0 w % and 10 w % of one or more sugars.

In particular embodiments, the medium comprises between 1.0 w % and 10 w % of one or more sugars selected from the list consisting of sucrose, maltose, and trehalose.

In particular embodiments, the cryopreservation medium envisaged herein comprises between 1.0 w % and 10 w % of sucrose. In particular embodiments, the medium does not comprise serum. In particular embodiments, the medium envisaged for use herein further comprises serum albumin, and/or hyaluronic acid.

The cryopreservation medium is envisaged to be of particular interest in the cryopreservation of multipotent cells which are adult stem cells selected from the group consisting of bone marrow, hematopoietic stem cells, skin stem cells, ocular stem cells, neural stem cells and cardiac stem cells.

In particular embodiments, the application relates to the use of a cryopreservation medium for the cryopreservation of stem cells or progenitor cells thereof, wherein said medium does not comprise dimethylsulfoxide (DMSO) or an arabinogalactan and comprises between 4 v/v % and 25 v/v % of propylene glycol and between 1.0 w/v % and 10 w/v % of sucrose.

The application further provides methods for the cryopreservation of stem cells and/or progenitor cells thereof, comprising the steps of (a) contacting said stem cells and/or progenitor cells with a cryopreservation medium, said cryopreservation medium comprising between 4 v/v % and 25 v/v % of propylene glycol; and between 1.0 w/v % and 10 w/v % of one or more sugars, preferably selected from sucrose, maltose, and trehalose; wherein said medium is characterized in that it does not comprise DMSO or an arabinogalactan; and (b) freezing said cells, thereby obtaining a frozen composition comprising said cells and said cryopreservation medium.

The methods envisaged herein are envisaged to be of particular use in the cryopreservation of stem cells which are multipotent cells. In particular embodiments, the stem cells and/or progenitor cells wherein said multipotent cells are adult stem cells selected from the group consisting of bone marrow stem cells, skin stem cells, ocular stem cells, neural stem cells and cardiac stem cells. In particular embodiments of the method the cryopreservation medium comprises between 1.0 w/v % and 10 w/v % of sucrose. In particular embodiments of the method, the cryopreservation medium (and the frozen composition) does not comprise serum. In particular embodiments of the method, the cryopreservation medium (and the frozen composition) further comprises serum albumin and/or hyaluronic acid.

In particular embodiments of the methods envisaged herein, step (a) comprises the addition of between 0.5 mL and 5 mL of said freezing medium per 1 million of said stem cells and/or progenitor cells.

In particular embodiments the methods envisaged herein further comprise the step of (c) thawing said frozen composition.

The application further provides a frozen medium comprising multipotent adult stem cells and/or progenitor cells thereof, and a cryopreservation medium; said cryopreservation medium not comprising DMSO or an arabinogalactan and comprising between 2 v/v % and 25 v/v % of propylene glycol and between 0.01 M and 1.0 M of a sugar.

In particular embodiments, the cryopreservation media envisaged herein have a low toxicity. The cryopreservation media and methods for using them described herein ensure high viability of the stem cells and/or progenitor cells thereof after thawing.

BRIEF DESCRIPTION OF THE DRAWINGS

The following description of the figures of specific embodiments of the invention is merely exemplary in nature and is not intended to limit the present teachings, their application or uses.

DETAILED DESCRIPTION OF THE INVENTION

Figure 1:
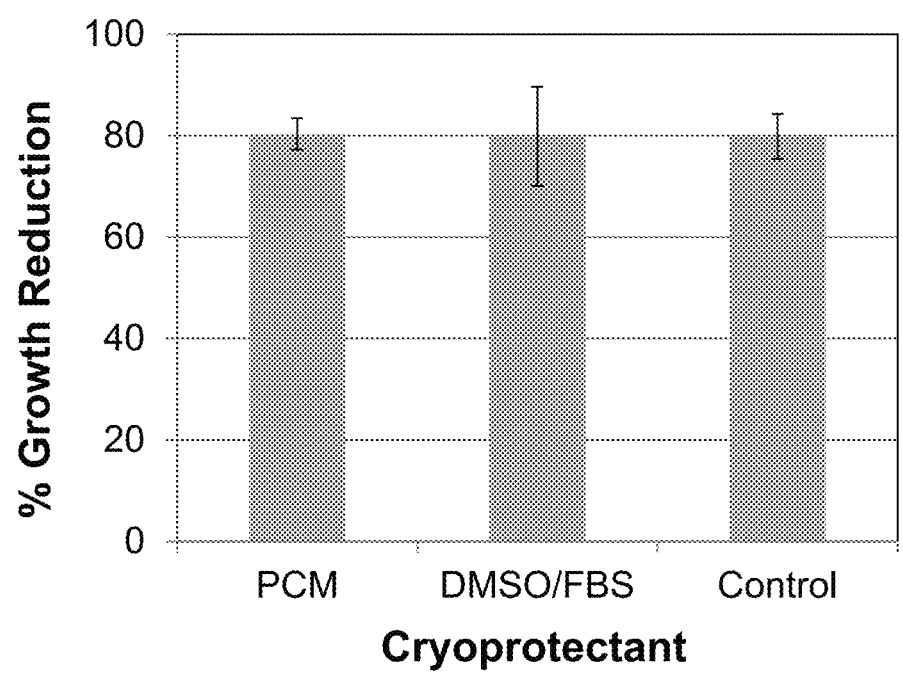
FIG. 1 Comparison of TGF-β-mediated growth inhibition in CT5.3-hTERT cells, showing the results for cells cryopreserved in PCM for 1 week, cells cryopreserved in DMSO/FBS for 1 week, and control cells.

While potentially serving as a guide for understanding, any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The values as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to ensure one or more of the technical effects envisaged herein. It is to be understood that each value as used herein is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the concepts described herein, including technical and scientific terms, have the meaning as commonly understood by one of ordinary skill in the art. By means of further guidance, definitions for the terms used in the description are included to better appreciate the teaching of the present disclosure. The terms or definitions used herein are provided solely to aid in the understanding of the teachings provided herein.

The term "stem cell" as used herein refers to either pluripotent or multipotent stem cells.

The term "pluripotent stem cell" as used herein refers to cells having the ability of self renewal and the potential to differentiate in any type of cell.

The term "multipotent stem cell" as used herein refers to stem cells which have the ability of self renewal and have the potential to differentiate into a limited number of cell types, typically within one category of cells such as blood cells (lymphocytes, monocytes, neutrophils), brain cells (neurons, glial cells etc.), bone cells (osteoblasts, osteoclasts etc)

The term "progenitor cell" as used herein refers to a stem cell which is able to differentiate into a certain type of cell and which has limited or no ability to self-renew.

The term, "slow freezing method" as used herein refers to a set of well-established techniques wherein a cell-containing sample is cooled at a controlled rate before final cryopreservation in liquid nitrogen or the like. Lethal intracellular freezing is avoided by cooling the cells slow enough to permit sufficient water to leave the cells during progressive freezing of the extracellular fluid. Preferably, the cooling rate is about −0.1° C./min to −10° C./min, more preferably between −0.2° C./min to −5° C./min, for example about 1° C. per minute. Slow-freezing is also known in the art as "Slow programmable freezing" and "Controlled-rate freezing", as opposed to vitrification methods.

The term "vitrification" as used herein refers to cryopreservation techniques wherein a sample is cooled at an extremely fast rate, e.g. by directly contacting the sample with liquid nitrogen, such that the sample is typically frozen within a few seconds. At such cooling rate the sample medium vitrifies, i.e. it forms an amorphous "solid state" instead of crystallizing.

Reference throughout this specification to "one embodiment" or "an embodiment" means that a particular feature, structure or characteristic described in connection with the embodiment is included in at least one embodiment envisaged herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are also envisaged herein, and form different embodiments, as would be understood by those in the art. For example, in the appended claims, any of the features of the claimed embodiments can be used in any combination.

Composition

Provided herein are compositions which can be used as a cryopreservation medium for the cryopreservation of stem cells and/or progenitor cells. The term "cryopreservation medium" as used herein refers to a liquid medium which can be used to treat the cells prior to freezing. It typically contains one or more cryoprotectants, which ensures the protection of the cells or tissues from freezing damage.

The composition described herein comprises propylene glycol as a cryoprotectant. Cryoprotectants can be permeating or non-permeating. Permeating cryoprotectants such as propylene glycol are able to permeate cell membranes.

The present inventors have found that the use of propylene glycol (1, 2-propanediol) in the absence of DMSO is surprisingly suitable for the cryopreservation of stem cells such as multipotent stem cells and/or progenitor cells thereof.

Accordingly, the composition described herein does not comprise DMSO but comprises propylene glycol, preferably in a concentration from about 4 v/v % (volume/volume percent) to about 25 v/v %. Particularly good results can be obtained when using propylene glycol in a concentration between 5 v/v % and 15 v/v %, for example about 11 v/v %.

The use of propylene glycol can allow for preparing cryopreservation media which are less toxic than conventional cryopreservation media comprising DMSO and ensure a high quality of cells after thawing.

The use of propylene glycol as a cryoprotectant has been found to be sufficient to adequately protect stem cells against freezing damage. However, in particular embodiments. The composition described herein may further comprise one or more cryoprotectants in addition to propylene glycol. In particular embodiments, the composition comprises one or more permeating cryoprotectants in addition to propylene glycol. In further embodiments, the composition may comprise ethylene glycol.

In certain embodiments, the composition comprises one or more non-permeating cryoprotectants, i.e. substances which do not permeate a cell membrane and protect a cell in freezing. Examples of suitable non-permeating cryoprotectants include, but are not limited to, sucrose, dextran, trehalose, percoll, polyethylene glycol, polyvinyl pyrrolidone, serum albumin, ficol, maltose, polyvinylalcohol (PVA) and the like. In particular embodiments, the composition does not comprise an arabinogalactan.

The present inventors have found that particularly good results were obtained when the composition comprises between 4 v/v % and 25 v/v % of propylene glycol, and between 1.0 w % and 10 w % of a sugar or a mixture of sugars. Preferably, the sugar or sugars are selected from the list consisting of sucrose, maltose, and trehalose.

In preferred embodiments, the composition comprises sucrose and/or serum albumin. In further particular embodiments, the composition does not comprise other permeating or non-permeating cryoprotectants. In certain embodiments, the composition comprises between 1.0 w/v % and 10 w/v % of sucrose, more particularly between 2 w/v % and 5 w/v % sucrose. In certain embodiments, the composition comprises between 0.1 w/v % (weight/volume percent) and 5 w/v % of serum albumin, more particularly between 0.5 w/v % and 3 w/v %, for example about 1.5 w/v %. In preferred embodiments, the serum albumin in the present composition is human and/or synthetic serum albumin.

In particular embodiments, the composition comprises propylene glycol, sucrose, and optionally serum albumin and/or hyaluronic acid. The present inventors have found that the combination of propylene glycol and sucrose provides a further improved medium for the cryopreservation of stem cells and/or progenitor cells, such as but not limited to multipotent stem cells. More particularly, the composition may comprise:

Between 4 v/v % and about 25 v/v % of propylene glycol; and

Between 1.0 w/v % and 10 w/v % of sucrose; and

Optionally, between 0.1 w/v % and 5 w/v % serum albumin; and

Optionally, between 0.05 w/v % and 0.5 w/v % hyaluronic acid.

The compositions described herein can be used as a cryopreservation medium without requiring the presence of serum in the composition. Therefore it can be ensured that the compositions do not pose a transmissible spongiform encephalopathy (TSE) risk. This is particularly relevant if the cells to be frozen are to be used for clinical and therapeutic applications. Moreover, the presence of xenogeneic sera during cryopreservation can alter the expression profiles and characteristics of the cells.

Thus, in preferred embodiments, the composition does not comprise serum. More particularly, in certain embodiments, the composition does not comprise any raw materials of direct human or animal origin, or materials that have been produced using materials of human or animal origin.

The composition typically is provided as an aqueous solution of the one or more cryoprotectants. More particularly, the cryoprotectants are preferably dissolved in a balanced electrolyte solution, more particularly a saline solution. The skilled person will understand that a typical solution will have an appropriate concentration of electrolytes (such as sodium, potassium, and/or chloride ions) to maintain a normal osmolality. Suitable saline solutions for use in cryopreservation are well known in the art. In particular embodiments, the saline solution is a phosphate-buffered saline solution (PBS). In particular embodiments, the composition comprises at least 70 w % of a (buffered) saline solution. In particular embodiments, the saline solution comprises a mixture of two or more of the following so as to ensure a buffering solution: Sodium Chloride, Potassium Chloride, Magnesium Sulfate, Potassium Phosphate, Calcium Chloride, and Sodium Bicarbonate. In further embodiments, the medium comprises, in addition to the components mentioned above, additional components such as energy substrates. In particular embodiments, the medium consists of the components recited above and does not contain further additives such as proteins. In particular embodiments, the cryoprotectant is dissolved in Human Tubal Fluid (HTF) medium, which is a synthetic defined medium specifically developed for use as culture medium for early embryo development and the processing of gametes. In particular embodiments, the composition described herein has a pH of between 6.9 and 7.5, more preferably between 7.2 and 7.4. The solution preferably comprises one or more buffers, for example a phosphate buffer.

Further provided herein is the use the present cryopreservation medium for the cryopreservation of stem cells and/or progenitor cells. A cryopreservation method involving the use of the present cryopreservation medium is described herein below.

Cryopreservation Method

Further provided herein is a method for the cryopreservation of stem cells and/or progenitor cells; or cultures and/or tissues comprising such cells. Whereas conventional cryoprotectants such as DMSO are known to be toxic to stem cells, the present methods envisages the use of propylene glycol, having a reduced toxicity. More particularly, the present methods comprise the steps of:

(a) contacting stem cells and/or progenitor cells with a cryopreservation medium, wherein said cryopreservation medium is a composition as described above; and
(b) freezing said stem cells and/or progenitor cells, thereby obtaining a frozen cell composition.

This will be explained further herein below.

In a first step, the present method involves contacting the cells with a cryopreservation medium as described above. Typically, this involves adding the cryopreservation medium to the cells, and mixing the cells with the medium. More particularly, water is removed from the cells and is replaced by the medium comprising the cryoprotectant which enters into the cell. Step (a) of the present method typically results in obtaining a (liquid) mixture of the cells in suspension in the medium. The stem cells and/or progenitor cells can be obtained by methods known in the art.

The cells are typically provided in a container prior to contacting with the cryopreservation medium. The term "container" as used herein refers to a storage system capable of holding a liquid. Suitable containers are well known in the art. Typically, the container has a volume between 1 mL and 50 mL, such as but not limited to tubes of 15 mL.

The methods described herein are of particular interest for the cryopreservation of cells which are not yet completely differentiated. In particular embodiments, the cells are multipotent stem cells, more particularly adult stem cells. In further particular embodiments, the cells are obtained from adult brain, bone marrow, blood vessels, skeletal muscle, skin, teeth, heart, gut, liver, or other adult tissues. In particular embodiments, the cells are selected from the group consisting of endodermal, urogenital, mesodermal or ectodermal origin.

In further particular embodiments, the stem cells of endodermal origin are pulmonary epithelial stem cells, gastrointestinal tract stem cells, pancreatic stem cells or hepatic oval cells and/or progenitor cells thereof. In particular embodiments, the cells of urogenital origin are either categorized as mammary and prostatic gland stem cells or ovarian and testicular stem cells and/or progenitor cells thereof. In particular embodiments, the cells of mesodermal origin are bone marrow cells, hematopoietic stem cells, stromal stem cells or cardiac stem cells and/or progenitor cells thereof. In particular embodiments, the cells of ectodermal origin are neural stem cells, skin stem cells or ocular stem cells and/or progenitor cells thereof.

In particular embodiments, the cells are not embryonic stem cells.

In preferred embodiments, between 0.5 mL and 5 mL of cryopreservation medium is added per one million cells, for example about 1 mL per million cells. However, it is envisaged that in certain embodiments, higher or lower amounts of cryopreservation medium can be used.

In certain embodiments, the cryopreservation medium may be added to the cells in step-wise increments of increasing concentration. This may reduce the risk of cellular osmotic shock associated with single-step addition.

The temperature of the cryopreservation medium when added to the cells preferably ranges from about 15° C. to 40° C. In certain embodiments, the temperature of the cryopreservation medium is about 37° C.

In preferred embodiments, the mixture of the cells and the cryopreservation medium is equilibrated prior to freezing the mixture. However, this incubation time must be limited to avoid damage to the cells. Thus, typically, the mixture is equilibrated for a time period of between 10 seconds and 5 minutes, typically between 20 seconds and 1.5 minutes, such as 30 seconds to 1 minute.

In a further step (b), the present method involves freezing of the cells. More particularly, the mixture comprising the cells is transferred to a freezing container, which is then transferred to subzero temperature. Suitable containers include, but are not limited to Mr. Frosty™ freezing containers from Thermo Scientific. Such containers typically provide for the stacking of tubes and can ensure that, by placing the container in a freezer, a fixed rate of cooling is achieved.

In preferred embodiments, the present method involves slow-freezing of the cells. Indeed, whereas cryopreservation is typically done via either slow-freezing or vitrification, these methods have different requirements regarding freezing solutions.

In particular embodiments, step (b) involves slow-freezing of the cells, wherein in a first step, the cells are cooled at a controlled rate to a temperature below −50° C., preferably below −70° C., more particularly to a temperature between −70° C. and −100° C.; typically followed by further cooling of the cells, e.g. by transfer of the cells to liquid nitrogen ($N_2$). In particular embodiments, the controlled rate is a cooling rate between −0.1° C./min and −10° C./min, preferably between −0.2° C./min to −5° C./min. In particular embodiments, the system is designed to achiever a rate of cooling of about 1° C./minute. Typically, the freezing container is put at a temperature of between −70° C. and −100° C., more particularly at −80° C. overnight to ensure slow freezing. Thereafter, the container comprising the mixture of the cells and the cryopreservation medium may be transferred to liquid nitrogen ($N_2$) at approximately −196° C.

The cells can remain in a cryogenic state for periods of days, weeks, months or years, for retrieval when the cells are required. When required, the cryopreserved cells are retrieved and thawed. Accordingly, in particular embodiments, the method described herein further comprises the step of (c) thawing the frozen composition, more particularly under conditions that maintain cell viability.

In particular embodiments, the container containing the cells can for instance be thawed in a bath of water, at a temperature of maximum 42° C., preferably between 10° C. and 40° C., for example about 37° C.

To reduce the mechanical destruction of the cells and preserve the post-thaw cell viability a thawing rate between about 10° C. and about 40° C. per minute, preferably between about 20° C. and about 40° C. per minute and for instance approximately 30° C. per minute may be used.

The methods described herein may allow for the cryopreservation of stem cells and/or progenitor cells, wherein the cells maintain a good viability after recovery. As used herein, the term "viability" refers to the number of living cells based on the presence of DNA and an intact cell membrane system. The viability can be measured by any methods known in the art and for instance using a Trypan blue internalization test or by measuring propidium iodide uptake. In particular embodiments, the viability of the recovered cells is at least 50%. In further embodiments, the viability of the recovered cells is at least 55%, at least 60%, at least 65%, at least 70%, at least 75%, at least 80%, at least 85%, at least 90%, or at least 95%. In further particular embodiments, the methods envisaged herein ensure that the stem cells and/or progenitor cells thereof display a limited amount of necrosis and apoptosis after thawing. In particular embodiments, necrosis and/or apoptosis is observed in less than 25% of the cells, more particularly less than 15%, most particularly less than 10% of the cells. The methods described herein may further ensure that the cells maintain their ability to differentiate into the envisaged cell type. This can be established by the determination of expression of lineage-specific markers. For instance, functional characterization of the mesenchymal stem cells may include induction of adipogenic, osteogenic and chondrogenic differentiation in vitro using commercially available differentiation kits and RT-PCR to detect lineage specific expression of mRNA, indicative for adipogenic, osteogenic and chondrogenic differentiation potential. Similarly, the quality of the undifferentiated stem cells can be tested by isolation of mRNA and testing on cell-specific markers. In particular embodiments, the ability to differentiate into a cell of the specified lineage is maintained, i.e. does not significantly differ from unprocessed cells.

In particular embodiments, the present method further comprises monitoring the quality of the cells after thawing. Several controls can be performed such as a sterility control, immunophenotype characterization, differentiation tests and an inspection of the morphology of the stem and/or progenitor cells.

In certain embodiments, the cells which are cryopreserved according to the methods described herein may be used for therapeutic purposes, more particularly in regenerative medicine.

Further provided herein is a frozen medium obtainable using the cryopreservation method as described herein. More particularly, the frozen medium comprises stem cells and/or progenitor cells, and a cryopreservation medium as described above. In certain embodiments, the cryopreservation medium comprises between 4 v/v % and 25 v/v % of propylene glycol; and between 1.0 w/v % and 10 w/v % of sucrose. Preferably, the frozen medium is obtained by slow-freezing. Such medium can be distinguished from a frozen medium obtained by vitrification via the crystalline nature of the frozen medium.

EXAMPLES

The following examples are provided for the purpose of illustrating the present invention and by no means are meant and in no way should be interpreted to limit the scope of the present invention.

1. Cryopreservation of Human Mesenchymal Stem Cells

1.1 Cryopreservation of Stem Cells

Culture-expanded human mesenchymal stem cells were harvested and centrifuged at 350×g for 5 minutes. Following removal of the supernatant, the freezing medium as described in Table 1 was added at a ratio of 1 mL for every 1 million cells. Aliquots of the mixture were pipetted into 1 mL cryovials, and immediately transferred to a controlled-rate freezer with a cooling rate of 1° C./min. Following overnight incubation, samples were stored in a liquid nitrogen tank for 2 weeks up to 6 months before thawing.

TABLE 1

| Cryopreservation medium | |
|---|---|
| 1,2-Propanediol | 1.558M or 11.4% v/v |
| Sucrose | 0.1M |
| Human serum albumin | 1.5% w/v |
| PBS | 82.6% v/v |

Cryopreserved cells were rapidly thawed by immersing the vials in a water bath set at 37° C. Afterwards, the cells were diluted in the growth medium used for their primary expansion. Cells were cultured until the desired cell number was reached.

1.2 Post-Thaw Analysis

From the next passage onwards (P1), cell count and post-thaw cell viability analysis was performed at the end of each passage using a cell counter. Population doubling time (PDT) during P1 was calculated by the equation PDT= (culture time*ln 2)/ln (cell number$_{harvested}$/cell number$_{seeded}$).

Viability of cells frozen with our cryopreservation medium was comparable to the viability of stem cells frozen with a DMSO containing medium, which is considered to be the gold standard. All values were higher than 80%. Also, post-thaw growth curve progression of cells cryopreserved in the two different media were comparable.

Functional characterization of the mesenchymal stem cells included induction of adipogenic, osteogenic and chondrogenic differentiation in vitro using commercially available differentiation kits. RT-PCR was performed to detect lineage specific expression of mRNA, indicative for adipogenic, osteogenic and chondrogenic differentiation potential. To test for the effect of the cryopreservation process on the undifferentiated stem cells, mRNA of cell-specific markers was isolated and analyzed using the same technique. Cells frozen in our DMSO-free medium were still able to express the lineage-specific markers.

2. Cryopreservation of Fibroblasts

Immortalized CT5.3-hTERT colon cancer-associated fibroblasts have been used to evaluate cellular function following cryopreservation with two different cryopreservation media:
1) a 10:90 (% V/V) mixture of dimethylsulfoxide (DMSO) and fetal bovine serum (FBS), as known in the art; and
2) a propylene glycol-based DMSO-free cryopreservation medium as described in Table 1 (hereafter referred to as "PCM").

Cancer-associated myofibroblasts express specific markers, including α-smooth muscle actin (α-SMA). Several studies have demonstrated that the cytokine transforming growth factor β (TGF-β) significantly increases the expression of α-smooth muscle actin (α-SMA), see e.g. Desmoulière et al. (*Journal of Cell Biology* 1993, 122, 103-111) and Hawinkels et al. (*Oncogene* 2014, 33, 97-107). Accordingly, α-SMA expression and cell proliferation are good indicators to assess the influence of cryoprotectants on CT5.3-hTERT cell functioning.

2.1 Experimental Setup

Briefly, early passage cells were cultured in routine culture medium (Dulbecco's Modified Eagle Medium (DMEM) containing 10% FBS, antibiotics and an antifungal product) at 37° C. in a humidified atmosphere with 5% $CO_2$. Semi-confluent cells were harvested by trypsinization and cell concentration was assessed using the trypan blue exclusion method.

Cells were resuspended in both freezing media at a concentration of one million cells per ml and transferred to cryovials. In turn, an overnight freezing step at −80° C. was performed using a Mr. Frosty™ container (available from Thermo Scientific), at a cooling rate of −1° C. per minute. Subsequently, the cryovials were transferred to liquid nitrogen.

The cells were thawed according to the standard protocol after 1 week (1 week protocol) and after 1 month (1 month protocol). In short, cells were removed from the liquid nitrogen and were transferred to a water bath at 37° C. Upon completion of thawing, a prewarmed culture medium was added dropwise. Next, the cells were centrifuged and the culture medium was replaced to remove traces of cryoprotectant. Finally, cells were seeded in culture flasks (T150) and allowed to grow for at least 2 passages in order to fully recover from the freeze/thaw cycle. The medium was refreshed every 2 days during culturing.

For the assessment the influence of the cryoprotectants, three groups of cells were used:
Cryopreserved cells using PCM medium;
Cryopreserved cells using DMSO/FBS medium; and
Cells cultured under routine culture (Control)

The cells of each group were treated with recombinant TGF-β (1 ng/ml) for 1 week. At the end of the experiment, cell concentration was measured using the sulforhodamine B (SRB) assay and an automated cell counter (trypan blue exclusion), respectively. Afterwards, cells were lysed with a detergent-based lysis buffer supplemented with phenylmethylsulfonyl fluoride (PMSF) and other protease inhibitors. Protein content was assessed by the bicinchoninic acid (BCA) test and concentrations were normalized, thus allowing for equal protein load for Western blot analysis. Expression of α-SMA was evaluated using a monoclonal HRP-coupled antibody, directed against this myofibroblast marker. In parallel, α-tubulin expression levels served as a loading control.

2.2 Results

1 Week Protocol

Figure 2:
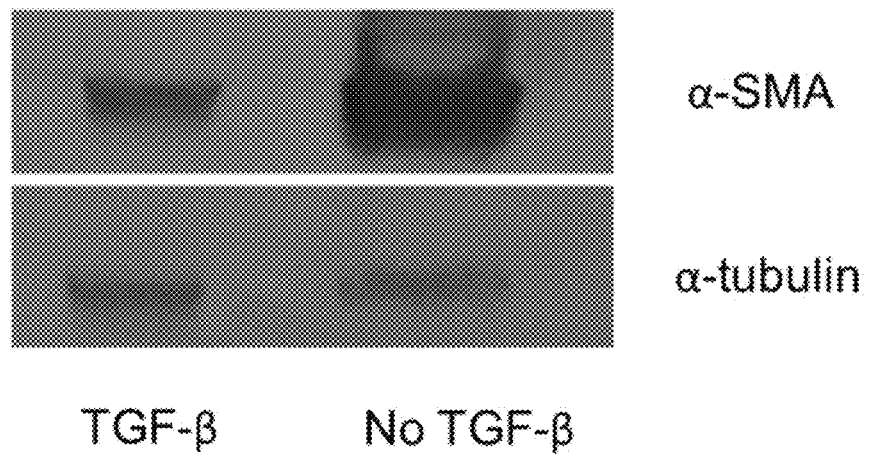
FIG. 2 Effect of TGF-β on α-SMA expression in CT5.3-hTERT cells.

In the control group, TGF-β was found to inhibit cell proliferation with 79.84+/−4.43 (n=3). Similar results were obtained for cells, frozen with either PCM (80.34+/−3.09%) or DMSO/FBS medium (79.86+/−9.78%) as shown in FIG. 1. Western Blot analysis revealed strong and comparable induction of α-SMA expression following TGF-β treatment in all three groups. An example of a Western blot is presented in FIG. 2 (control cells treated with and without TGF-β).

1 Month Protocol

Figure 3:
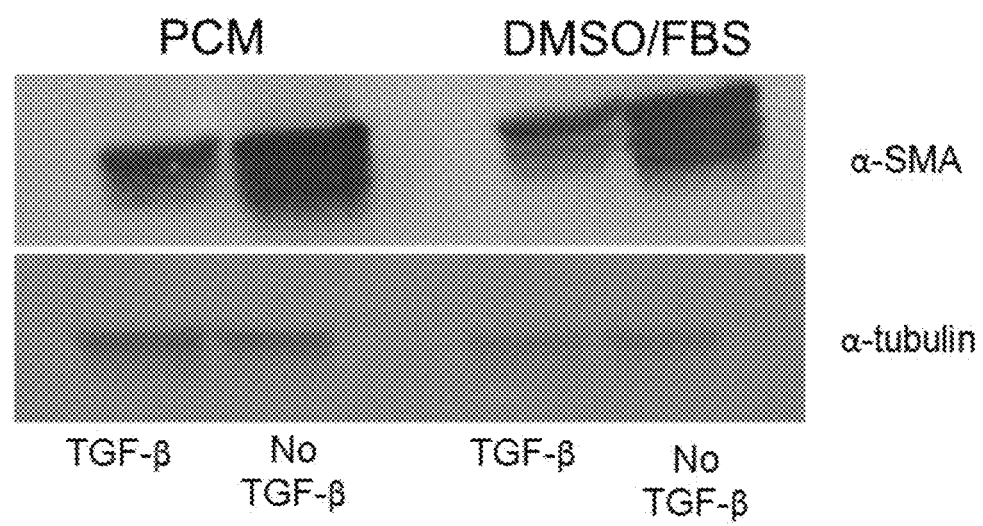
FIG. 3 Effect of TGF-β on α-SMA expression in CT5.3-hTERT cells, cryopreserved in PCM and DMSO/FBS, respectively.

Growth inhibition and α-SMA expression was investigated in cells which were subjected to cryopreservation for 1 month. Although a somewhat higher reduction was observed for DMSO/FBS cells (88.38+/−0.03%), the PCM medium (81.38+/−8.19%) was found to yield identical growth inhibition as the control. Again, Western blot analysis confirmed strong induction of α-SMA protein expression in all three groups. An example of results obtained for cells which treated with the two studied cryoprotectants is shown in FIG. 3.

2.3 Conclusion

Experimental data from cell proliferation and Western blot studies have demonstrated that propylene glycol-based media as described herein are an excellent substitute for DMSO-based cryopreservation media. Cellular functioning of an immortalized colon cancer cell line was not affected by the type of cryopreservation medium or by the duration of cryopreservation.

This demonstrates that immortalized cell lines can be cryopreserved under serum-free conditions using a propylene glycol-based cryopreservation medium as described herein. Importantly, the time of freezing does not interfere with cell functioning.

It is noted that further cryopreservation tests on (MSC)-hTERT mesenchymal stem cells using the above-mentioned DMSO/FBS and PCM also show similar results for both cryopreservation media. Although TGF-β was found not to alter α-SMA expression, a 2-3 fold induction of cell proliferation was observed in all 3 groups (control, DMSO/FBS, and PCM).

The invention claimed is:

1. A non-vitrified frozen composition comprising stem cells and/or progenitor cells thereof, and a cryopreservation medium; said cryopreservation medium not comprising DMSO or an arabinogalactan and comprising between 5 v/v % and 15 v/v % of propylene glycol as a permeating cryoprotectant and between 1.0 w/v % and 10 w/v % of one or more sugars, wherein, after recovery, said cells have a post-thaw viability of at least 80%.

2. The non-vitrified frozen composition according to claim 1, wherein said stem cells are multipotent stem cells.

3. The non-vitrified frozen composition according to claim 1, wherein said stem cells and/or progenitor cells are stem cells selected from the group consisting of bone marrow stem cells, hematopoietic stem cells, skin stem cells, ocular stem cells, neural stem cells, and cardiac stem cells.

4. The non-vitrified frozen composition according to claim 1, wherein said one or more sugars are selected from the group consisting of sucrose, maltose, and trehalose.

5. The non-vitrified frozen composition according to claim 1, wherein said cryopreservation medium comprises between 1.0 w/v % and 10 w/v % of sucrose.

6. The non-vitrified frozen composition according to claim 1, wherein said cryopreservation medium does not comprise serum.

7. The non-vitrified frozen composition according to claim 1, wherein said cryopreservation medium further comprises serum albumin and/or hyaluronic acid.

8. The non-vitrified frozen composition according to claim 1, wherein propylene glycol is the only permeating cryoprotectant in the cryopreservation medium.

* * * * *